United States Patent
Cohen et al.

(10) Patent No.: US 11,974,817 B2
(45) Date of Patent: May 7, 2024

(54) CATHETER REPRESENTATION VIA VOXELS WITHIN ORGAN

(71) Applicant: Biosense Webster (Israel) Ltd., Yokneam (IL)

(72) Inventors: Benjamin Cohen, Haifa (IL); Lior Zar, Poria Illit (IL); Natan Sharon Katz, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 627 days.

(21) Appl. No.: 17/163,978

(22) Filed: Feb. 1, 2021

(65) Prior Publication Data

US 2022/0241022 A1 Aug. 4, 2022

(51) Int. Cl.
*A61B 34/20* (2016.01)
*A61B 90/00* (2016.01)
*G06T 15/08* (2011.01)
*G06T 17/20* (2006.01)

(52) U.S. Cl.
CPC ............. *A61B 34/20* (2016.02); *A61B 90/37* (2016.02); *A61B 90/39* (2016.02); *G06T 15/08* (2013.01); *G06T 17/205* (2013.01); *A61B 2034/2065* (2016.02); *A61B 2034/2068* (2016.02); *G06T 2210/36* (2013.01); *G06T 2210/41* (2013.01)

(58) Field of Classification Search
CPC ......... A61B 34/20; A61B 90/37; A61B 90/39; G06T 15/08; G06T 17/205
See application file for complete search history.

(56) References Cited

U.S. PATENT DOCUMENTS

| | | |
|---|---|---|
| 6,814,733 B2 | 11/2004 | Schwartz et al. |
| 6,961,602 B2 | 11/2005 | Fuimaono et al. |
| 6,997,924 B2 | 2/2006 | Schwartz et al. |
| 7,156,816 B2 | 1/2007 | Schwartz et al. |
| 7,536,218 B2 | 5/2009 | Govari et al. |

(Continued)

FOREIGN PATENT DOCUMENTS

| | | |
|---|---|---|
| EP | 3332709 A1 | 6/2018 |
| WO | 2016/089870 A1 | 6/2016 |
| WO | 2019/027517 A2 | 2/2019 |

OTHER PUBLICATIONS

Extended European Search Report dated Jul. 4, 2022 for European Patent Application No. 22154156.8.

*Primary Examiner* — David Bilodeau
(74) *Attorney, Agent, or Firm* — Volpe Koenig (57) ABSTRACT

Methods, devices, and systems for acquiring the volume of a catheter are disclosed. The system may comprise a catheter and a processor. The processor may be configured to receive a voxel grid comprising a plurality of voxels and a plurality three-dimensional coordinates of a location of a catheter. The processor may render the catheter on a display using the three-dimensional coordinates, wherein the catheter rendering comprises a plurality of shaded pixels. The processor may identify coordinates of one or more voxels of the voxel grid which overlap with at least one shaded pixel and mark the voxels of the voxel grid which overlap with at least one shaded pixel. As such, a voxel trail may be created wherever a catheter moves. The voxel trail may be used to define an internal volume within which the catheter is positioned, such as a chamber of a heart, blood vessel, or valve.

19 Claims, 7 Drawing Sheets

(56) References Cited

U.S. PATENT DOCUMENTS

| | | | |
|---|---|---|---|
| 7,756,576 B2 | 7/2010 | Levin | |
| 2008/0119727 A1* | 5/2008 | Barbagli | A61B 8/12 |
| | | | 600/437 |
| 2009/0148012 A1 | 6/2009 | Altmann et al. | |
| 2011/0125150 A1* | 5/2011 | Deno | A61B 5/6844 |
| | | | 606/34 |
| 2011/0201915 A1* | 8/2011 | Gogin | A61B 6/5288 |
| | | | 600/407 |
| 2014/0222370 A1 | 8/2014 | Manzke et al. | |
| 2017/0330487 A1* | 11/2017 | Harlev | G16H 15/00 |
| 2018/0146883 A1* | 5/2018 | Govari | A61B 6/5247 |
| 2019/0365474 A1* | 12/2019 | Jaramaz | G06T 19/20 |
| 2021/0137488 A1* | 5/2021 | Yellin | A61B 8/13 |
| 2023/0098497 A1* | 3/2023 | Laby | A61B 34/10 |
| | | | 606/130 |

* cited by examiner

CATHETER REPRESENTATION VIA VOXELS WITHIN ORGAN

FIELD OF INVENTION

This invention relates to constructing a model of an internal volume. More particularly, this invention relates to constructing a model of an anatomical structure.

BACKGROUND

Medical applications may call for constructing a model of an anatomical structure, such as a chamber of a heart. In current implementations, a catheter may be moved within the chamber of the heart and the location of the catheter may be continually recorded by a tracking system. Each of the recorded locations, or "points" may be added to a "point cloud" representing the chamber of the heart. A volume of voxels may then be constructed from the point cloud, and a mesh model may then be constructed from the volume. However, current implementations are time and resource intensive. As such, it would be desirable to have more efficient process for constructing a model of an anatomical structure.

SUMMARY

Methods, devices, and systems for constructing an internal volume from which a model may be created are disclosed. The system may comprise a catheter and a processor. The processor may be configured to receive a voxel grid comprising a plurality of voxels and a plurality three-dimensional coordinates of a location of a catheter. The processor may render the catheter on a display using the three-dimensional coordinates, wherein the catheter rendering comprises a plurality of shaded pixels. The processor may identify coordinates of one or more voxels of the voxel grid which overlap with at least one shaded pixel and mark the voxels of the voxel grid which overlap with at least one shaded pixel. As such, a voxel trail may be created wherever a catheter moves. The voxel trail may be used to define an internal volume within which the catheter is positioned, such as a chamber of a heart, blood vessel, or valve. The processor may be configured to generate a mesh representing a surface of the internal volume by applying a mesh-generating algorithm to a volume that includes the voxels marked as occupied.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
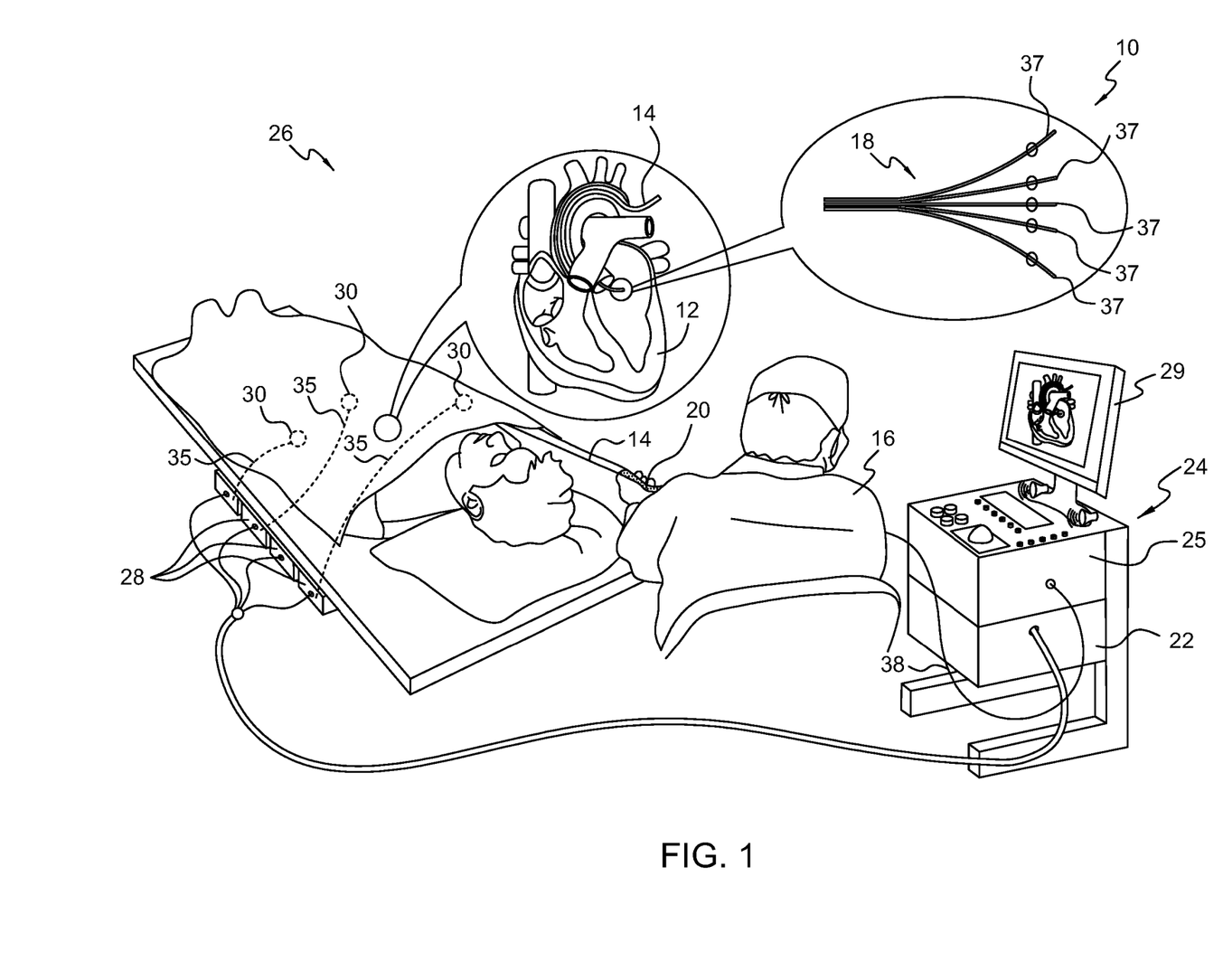
FIG. 1 is a schematic, pictorial illustration of a system for performing procedures on a heart of a living subject using a cardiac catheter having multiple branches, according to an exemplary embodiment.

FIG. 1 is a schematic, pictorial illustration of a system 10 for performing procedures on a heart 12 of a living subject, according to an embodiment. The system 10 may comprise a catheter 14 and a control console 24. One commercial product embodying elements of the system 10 is available as the CARTO® 3 System, available from Biosense Webster, Inc., 3333 Diamond Canyon Road, Diamond Bar, California 91765.

The catheter 14 may be used for any suitable therapeutic and/or diagnostic purposes, such as anatomical mapping of a cavity in a heart 12. The catheter 14 may be a multi-electrode catheter having an elongated body with multiple branches 37, each having mapping and location sensing capabilities. The catheter 14 may further comprise a handle 20, having controls which enable an operator 16, who is typically a physician, to steer, position and orient the distal end of the catheter 14 and the location and orientation of the branches 37 as necessary. The catheter described in U.S. Pat. No. 6,961,602, having five branches, is suitable for use as the catheter 14. This catheter is available as the Pentaray™ catheter or probe from Biosense Webster.

In some embodiments, the catheter 14 comprises an elongated body having a proximal end, a distal end, and at least one lumen extending longitudinally therethrough, and a mapping assembly mounted at the distal end of the catheter body and comprising at least two branches 37. Each branch 37 has a proximal end attached at the distal end of the catheter body and a free distal end. Each branch 37 comprises a support arm having shape memory, a non-conductive covering in surrounding relation to the support arm, at least one location sensor 41 (FIG. 2) mounted in the distal end of the branch 37, one or more electrodes mounted on the distal end of the branch 37 and electrically isolated from the support arm, and one or more electrode lead wires extending within the non-conductive covering, each electrode wire being attached to a corresponding electrode. In some embodiments, additional location sensors (not shown) may be disposed on the shaft of the catheter 14 proximal to the branches 37.

The catheter 14 may be percutaneously inserted by the operator 16 through the patient's vascular system into a chamber or vascular structure of the heart 12. The operator 16 may bring the catheter's distal tip 18 in contact with the heart wall at a desired mapping site. The distal end of the catheter 18 may then collect measurements. The collected measurements may be referred as "points." Each point comprises a three-dimensional coordinate on the tissue of cavity and a respective measurement of some physiological property that is measured at this coordinate.

Additionally, or alternatively, ablation energy and electrical signals may be conveyed to and from the heart 12 through one or more optional ablation electrodes located at or near the distal tip 18 through a cable to the console 24. Pacing signals and other control signals may be conveyed from the console 24 through the cable 38 and the one or more ablation electrodes to the heart 12.

Wire connections 35 may link the console 24 with body surface electrodes 30 and other components of a positioning sub-system. A temperature sensor 43 (FIG. 2), such as a thermocouple or thermistor, may be mounted on or near the distal tip 18.

The console 24 may comprise one or more ablation power generators 25. The catheter 14 may be adapted to conduct ablative energy to the heart using any known ablation technique, including but not limited to, radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The processor 22 may be an element of a positioning system 26 of the system 10 that measures location and orientation coordinates of the catheter 14.

In some embodiments, the positioning system 26 may comprise a magnetic position tracking arrangement that determines the position and orientation of the catheter 14 by generating magnetic fields in a predefined working volume in its vicinity and sensing these fields at the catheter using field generating coils 28 and may include impedance measurements, as taught, for example in U.S. Pat. No. 7,756,576, which is herein incorporated by reference. The positioning system 26 may be enhanced by position measurements using the impedance measurements described in U.S. Pat. No. 7,536,218, which is herein incorporated by reference.

As noted above, the catheter 14 is coupled to the console 24, which enables the operator 16 to observe and regulate the functions of the catheter 14. Console 24 includes a processor 22. The processor 22 may be coupled to display 29. The signal processing circuits may receive, amplify, filter, and digitize signals from the catheter 14, including signals generated by the above-noted sensors and a plurality of location sensing electrodes (not shown) located on the catheter 14. The digitized signals may be received and used by the console 24 and the positioning system 26 to compute the position and orientation of the catheter 14 and to analyze the electrical signals from the electrodes.

In some embodiments, the processor 22 may be a computer, and may be programmed in software to carry out the functions described herein. For example, in some embodiments, the processor 22 is a programmed digital computing device comprising a central processing unit (CPU), a graphics processing unit (GPU), a random access memory (RAM), non-volatile secondary storage, such as a hard drive or CD ROM drive, network interfaces, and/or peripheral devices. Program code, including software programs, and/or data are loaded into the RAM for execution and processing by the CPU and/or GPU, and results are generated for display, output, transmittal, or storage, as is known in the art. The software code may be downloaded to the computer in electronic form over a network, or it may be provided and/or stored on non-transitory tangible media, such as magnetic, optical or electronic memory.

Figure 2:
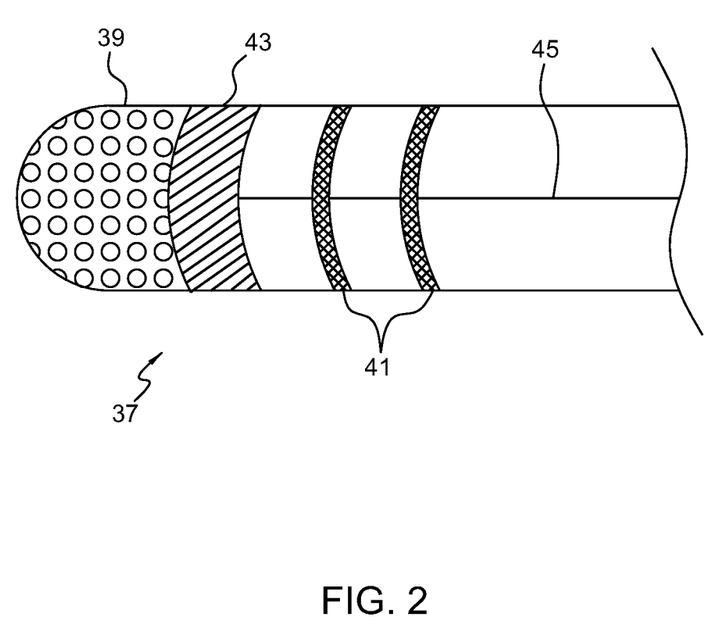
FIG. 2 is a is a detailed view of one of the branches of the catheter shown in FIG. 1, according to an exemplary embodiment.

FIG. 2 is a detailed view of one of the branches 37 of FIG. 1, showing an electrode configuration, according to an embodiment. The electrode configuration may comprise a tip electrode 39, two ring electrodes 41, and a temperature sensor 43. The tip electrode 39 may be configured for both sensing and ablation. The temperature sensor 43 may be used when the catheter 14 is in an ablation mode. The two ring electrodes 41 may be configured as sensing electrodes to detect electrophysiologic signals in the heart. However, as will be appreciated by one having ordinary skill in the art, the sensing electrodes and ablation electrodes may vary in number, configuration, and distribution in many combinations. One or more cables 45 may communicate signals between the electrodes, sensors, and the console 24. With multiple electrodes distributed in several branches 37, it is possible to collect signals from many locations simultaneously.

In current systems, a catheter, such as the catheter 14 described above, is moved within the chamber or within an adjoining blood vessel and the location of the catheter 14 is continually recorded. The processor 22 may receive the respective coordinates of a plurality of locations within a chamber of a heart. For example, as described above with respect to FIG. 1, a CPU may receive coordinates from a location-ascertaining routine, which ascertains the location of the distal end of the catheter 14 as the distal end is moved within the chamber. Each coordinate may be referred to as a "point" and the collection of coordinates may be referred to as a "point cloud." The point cloud may include hundreds, thousands, or tens of thousands of points, along with gaps in which no points are present.

The CPU may provide a catheter tree to the GPU. The catheter tree may comprise a collection of splines, each spline comprising a continuous curve which is formed so as to pass through a plurality of points. The plurality of points from which a spline is formed may be points (recorded locations) along a physical part of the catheter 14. Therefore, each spline may represent a physical part, such as a branch 37, of the catheter 14. In some embodiments, the plurality of points of a spline are 1-2 mm apart from each other. As used herein, a voxel grid is a regularly spaced, three-dimensional grid and a voxel represents a data point on a voxel grid. In current implementations, the processor 22 may use the catheter tree to determine volume acquisition by using a voxel to cylinder collision test and/or a voxel to sphere collision test, as briefly explained in the following paragraph.

In current implementations, each spline may be associated with a branch radius. The branch radius may correspond to the radius of a branch 37 of the catheter 14. Using the branch radius and a plurality of points of the spline, the processor 22 may create a cylinder. The processor 22 may create a cylinder for each spline. The processor 22 may overlay the cylinders representing branches 37 of the catheter 14 onto a voxel grid and perform a collision test between the cylinders and voxels of the voxel grid. In other words, the processor 22 may determine which voxels overlap with or are inside a cylinder. If a voxel overlaps with or is inside a cylinder, the processor 22 marks the voxel as occupied.

In current implementations, each spline tip may be associated with a tip radius. The tip radius may correspond to the radius of the tip of a branch 37. Using the tip radius and one or more points of the spline tip, the processor 22 may create a sphere. The processor 22 may create a sphere for each spline. The processor 22 may overlay the spheres representing the branch tips onto the voxel grid and perform a collision test between the spheres and voxels of the voxel grid. In other words, the processor 22 may determine which voxels overlap with or are inside a sphere. If a voxel overlaps with or is inside a sphere, the processor 22 may mark the voxel as occupied.

Using this process, voxels corresponding to the current location of the catheter may be determined. The catheter may be moved throughout an internal volume in order to define the internal volume. The internal volume may be an anatomical cavity, such as a chamber of the heart. The processor 22 may be configured to generate a mesh representing a surface of the volume by applying a mesh-generating algorithm to a volume that includes the first voxels and the subset of the second voxels. The processor 22 may be further configured to display the mesh on the display.

This current implementation is both time and resource intensive. For example, the Pentaray™ catheter comprises five branches about 10 mm in length. The collision detection test for a voxel and a cylinder requires about 100 floating point operations. As a result, a total of 5,000 floating point operations may be necessary. Further, every time the catheter moves, which is frequently (e.g., every 16 ms), the CPU must provide updated points to the GPU and the points must be converted into voxel space.

Figure 3A:
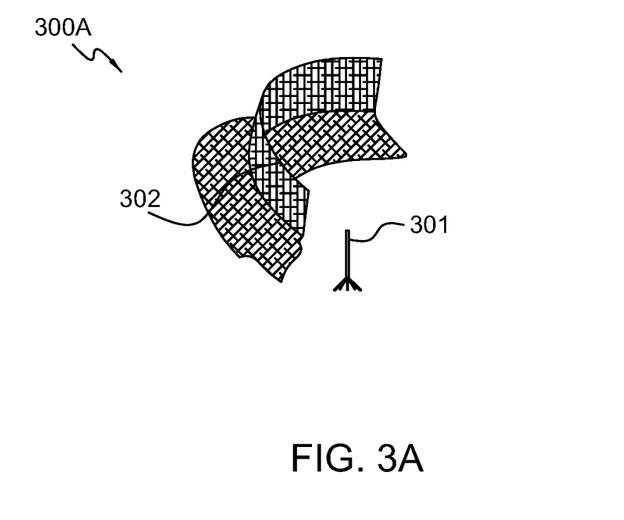
FIGS. 3A and 3B are schematic illustrations of a method for generating a volume of voxels, according to an exemplary embodiment.
Figure 3B:
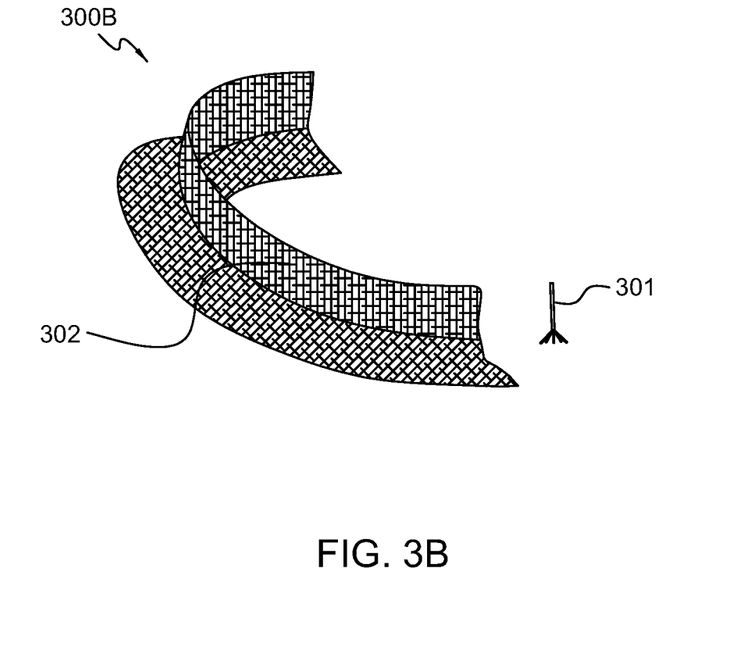

FIGS. 3A and 3B are schematic illustrations 300A and 300B, respectively, of a voxel trail of the catheter produced in accordance with the current implementation. The current implementation is time and resource intensive, as discussed above, creating a time delay between the rendering of the catheter 301 and the voxel trail 302.

Figure 4:
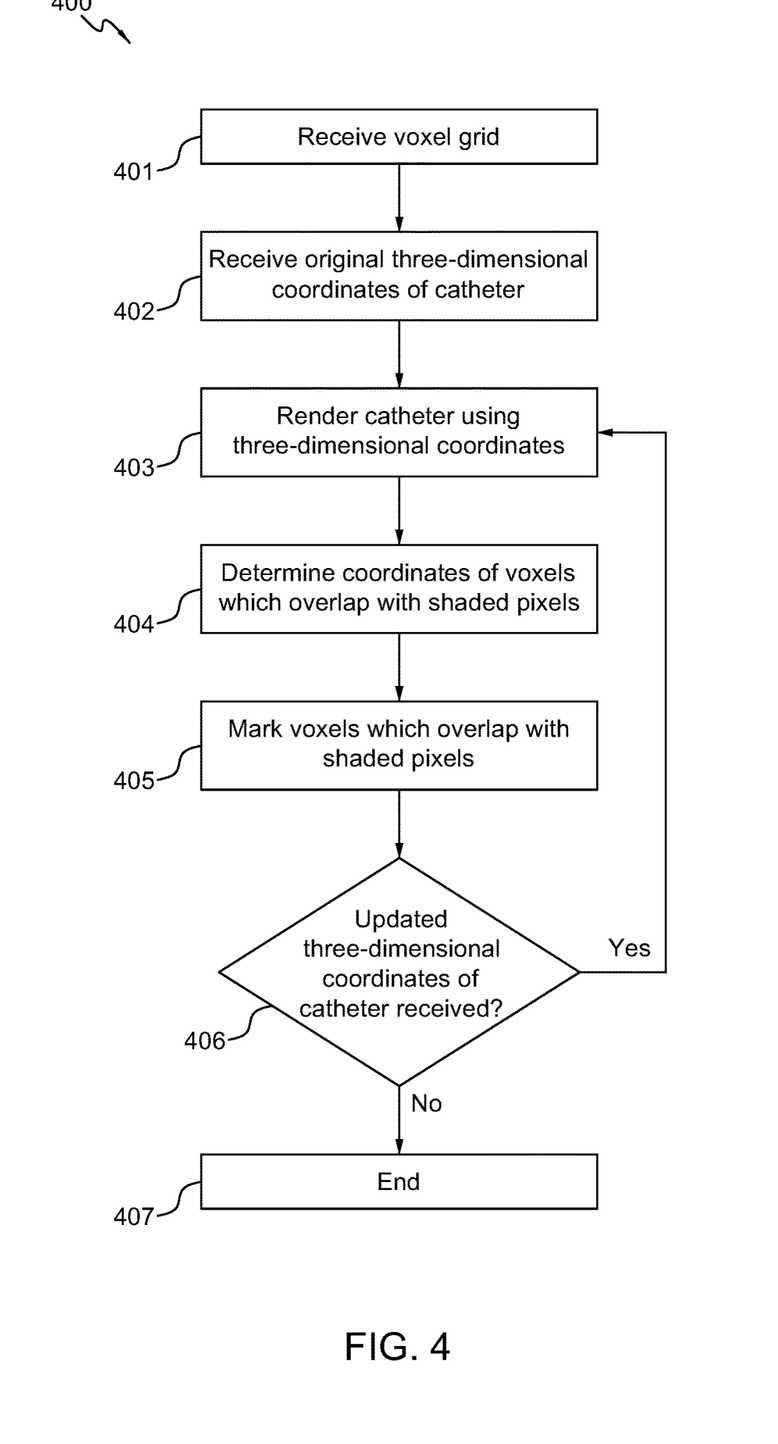
FIG. 4 is a flow diagram for a method for generating a volume of a voxels, according to an exemplary embodiment.

FIG. 4 is method for generating a volume of a catheter 400, according to an embodiment. The method 400 may be performed on the system 10 for performing procedures on a heart 12 of a living subject, as described above. However, as will be appreciated by one having ordinary skill in the art, the method 400 described herein may be implemented on computer systems utilized for a variety of purposes.

At 401, the processor 22 defines a voxel grid for a volume. The voxel grid may have any suitable shape. In some embodiments, the voxel grid may be a three-dimensional grid shape, such as a cubic shape. In some embodiments, the voxel grid may be defined by the CPU. For example, the CPU may determine the voxel grid using an algorithm, such as a fast anatomical mapping (FAM) algorithm. The CPU may define the volume as discrete number of voxels. The CPU may further define the dimensions for each voxel. By way of example only, the voxel grid may comprise 256× 256×256 voxels and the dimensions of each voxel may be 0.8×0.8×0.8 mm. Defining the voxel grid and voxel dimensions may be a one-time operation which does not have to be repeated subsequently during the procedure, as in current implementations. After defining the voxel grid and the dimensions of each voxel, the CPU may send this information to the GPU. The CPU may also send the catheter tree information to the GPU at 401. Alternatively, the CPU may provide the catheter tree information to the GPU before the process begins.

At 402, after the catheter has been inserted into the patient, the processor 22 receives a plurality of three-dimensional coordinates of the catheter 14. For example, as described above with reference to FIG. 1, the coordinates may be ascertained from a location-ascertaining routine, which ascertains the locations of the distal end of the catheter 26 as the distal end is moved within the chamber.

At 403, the processor 22 uses the coordinates corresponding to the location of the catheter 14 and the known catheter tree information to render the catheter 14 on the display 29. The GPU of the processor 22 may be used to render the catheter 14. In some embodiments, the GPU may utilize one or more programs, including but not limited to a vertex shader, a rasterizer, and a pixel shader, for rendering the catheter 14 on the display 29. The vertex shader may receive the original three-dimensional coordinates of the catheter 14 and transform the three-dimensional coordinates into a two-dimensional coordinate which appears on the screen, as well as a depth value for the Z-buffer. The vertex shader may manipulate properties such as position, color and texture coordinates. The output of the vertex shader may be passed to the rasterizer. The rasterizer may determine the pixels covered by a primitive (e.g., a triangle) and interpolate the output parameters of the vertex shader for each covered pixel. For each sample of the pixels covered by a primitive, a "fragment" is generated. The output of the rasterizer may then be given to the pixel shader, also known as a fragment shader. The pixel shader may shade a plurality of pixels in a pixel grid to create a two-dimensional rendering of the catheter 14 which corresponds to a three-dimensional position of the catheter on the screen. Specifically, the pixel shader may dictate the color, brightness, contrast, and other characteristics of the pixels. However, as will be appreciated by one having ordinary skill in the art, rendering of the catheter may comprise various different methods.

At 404, the processor 22 determines, the coordinates of each voxel which overlaps with a shaded pixel of the catheter rendering. In some embodiments, the processor 22 determines the coordinates of a voxel which overlaps with a shaded pixel of the catheter rendering using Equation 1, where $\overline{V}$ is the voxel coordinates (e.g., (i, j, k)), int3 refers to the return value (three integers), PixelPosition is a point associated with a shaded pixel (e.g., (x, y, z)), and VoxelSize is the size of each voxel as determined in 401 (e.g., 0.8 mm×0.8 mm×0.8 mm).

$$\overline{V} = int3\left(\frac{PixelPosition}{VoxelSize}\right) \qquad \text{Eq. 1}$$

At 405, the processor 22 marks one or more voxels which overlap with the pixels of the catheter rendering and designates such voxels as occupied. As such, once the catheter 14 has moved throughout the entirety of a chamber, the marked voxels may represent a sub-volume of the chamber.

At 406, if the processor 22 receives updated three-dimensional coordinates of the catheter 14, the process returns to 403. If updated three-dimensional coordinates of the catheter 14 are not received, the process ends at 407.

Figure 5A:
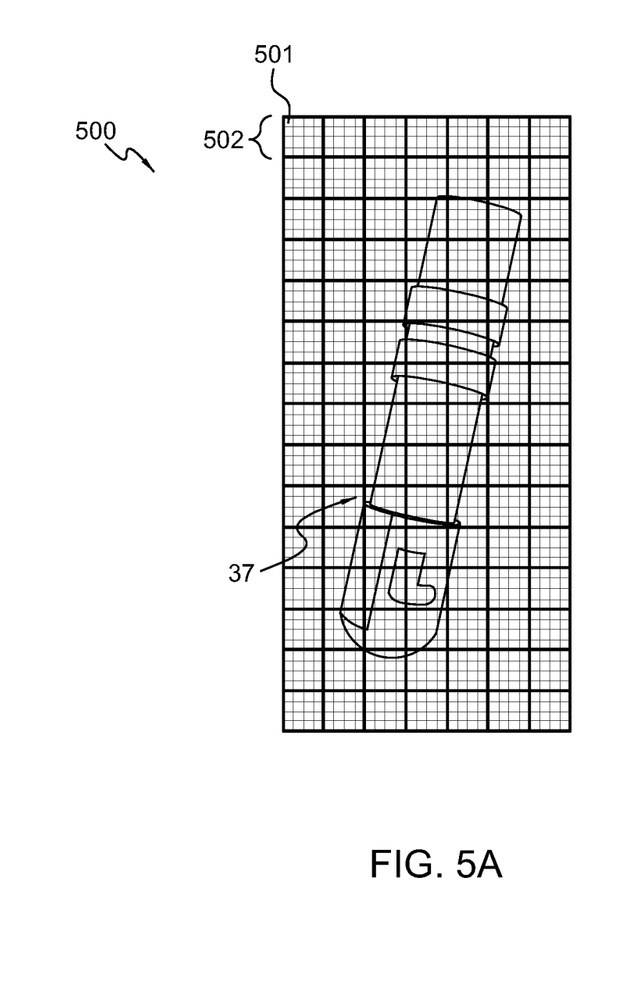
FIG. 5A is an illustration of a catheter with respect to a voxel grid and a pixel grid, according to an exemplary embodiment.

FIG. 5A is a two-dimensional illustration 500 of a branch 37 of a catheter in relation to a voxel grid (a three-dimensional grid comprised of voxels 502) and a pixel grid (a two-dimensional grid comprised of pixels 501). The voxel grid comprises a plurality of voxels 502 denoted by the thicker lines and the pixel grid comprises a plurality of pixels 501 denoted by the thinner lines, as described above. In the illustrated embodiment, the size of the pixels 501 making up the pixel grid are smaller than the voxels 502 making up the voxel grid. However, as will be appreciated by one having ordinary skill in the art, the size of the pixels 501 and the size of the voxels 502 may be the same or the size of the voxels 502 may be smaller than the size of the pixels 501.

Figure 5B:
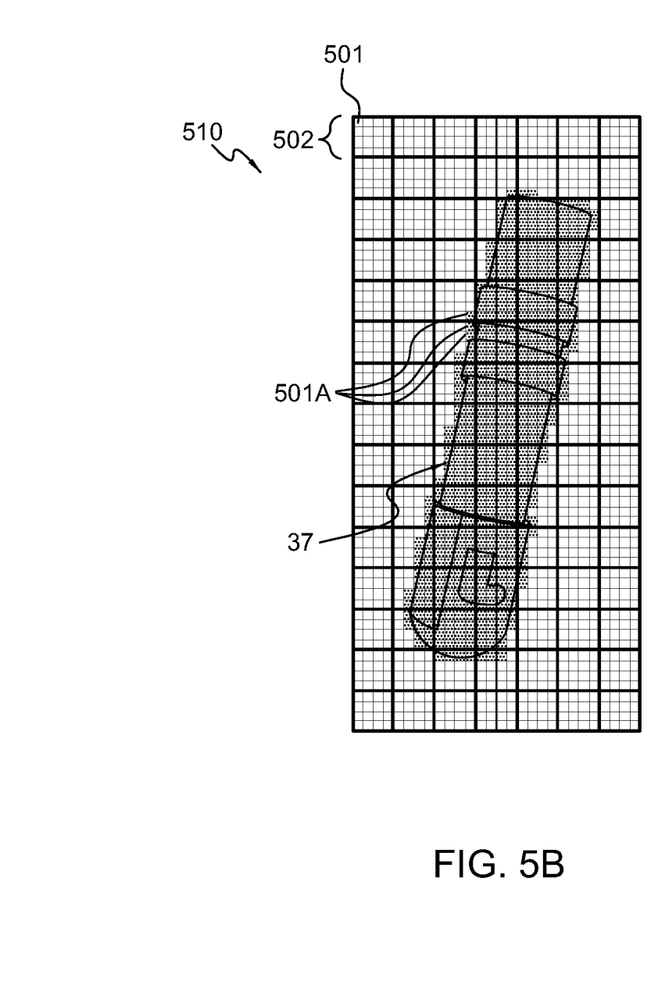
FIG. 5B is a rendering of the catheter of FIG. 5A with the occupied pixels marked, according to an exemplary embodiment.

FIG. 5B is a two-dimensional illustration 510 of the branch 37 of FIG. 5A, where the pixels that the catheter occupies are marked 501A, as described above with respect to 403 above. In the embodiment illustrated in FIG. 5B, the marked pixels 501A comprise the same color, brightness, and contrast. However, as will be appreciated by one having ordinary skill in the art, each of the marked pixels 501A may comprise different colors, brightness contrast, and the like.

Figure 5C:
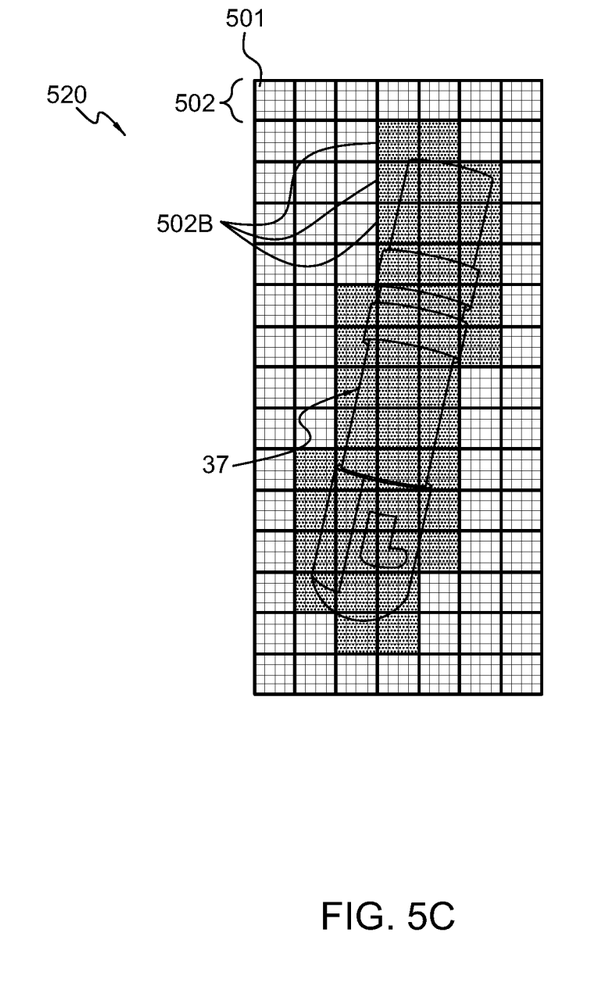
FIG. 5C is a rendering the catheter of FIG. 5B with the occupied voxels marked, according to an exemplary embodiment.

FIG. 5C is a two-dimensional illustration 520 of the branch 37 of FIG. 5A, where voxels 502A of the plurality of voxels 502 which overlap with at least one shaded pixel 501A of FIG. 5B are marked, as described above with respect to 404 and 405, The processor 22 may optionally apply one or more algorithms to optimize the volume acquisition of the catheter 14. For example, if there is a voxel that is surrounded by marked voxels on all sides, an algorithm may identify and mark the voxel as occupied. Additionally, or alternatively, a known chamber wall may be used to determine that reading of voxels identified outside of the chamber wall are not accurate readings.

This disclosed method 400 is less time and resource intensive than the current implementation. For example, in the Pentaray™ catheter comprising six splines about 10 mm in length, the points on the spline are about 0.5 mm apart. Therefore about 20 points per spline are required, resulting in 120 different pixels. The collision test for voxels and pixels requires 3 floating point operations. As such, a totally of about 360 floating point operations are required, much less than the thousands typically required in the current implementation. Further, the disclosed method 400 may be conducted entirely using the GPU of the processor 22. By operating in the GPU only, it is not necessary to upload and download information during the CPU and the GPU multiple times throughout the method.

Figure 6A:
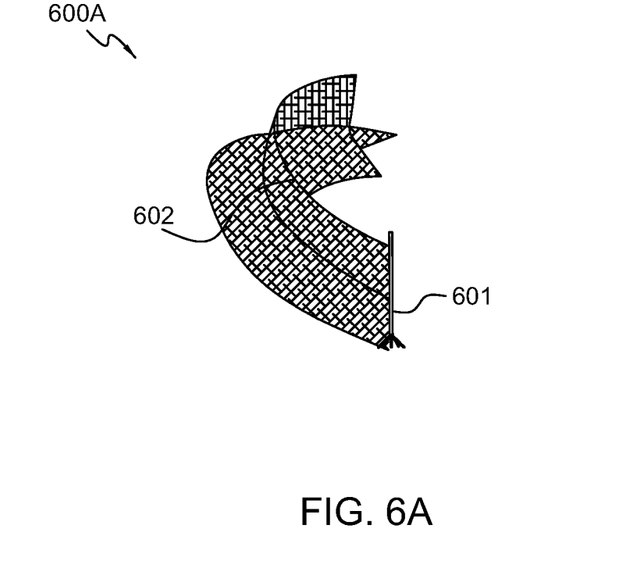
FIGS. 6A and 6B are schematic illustrations of various aspects of the method of FIG. 4, according to an exemplary embodiment.
Figure 6B:
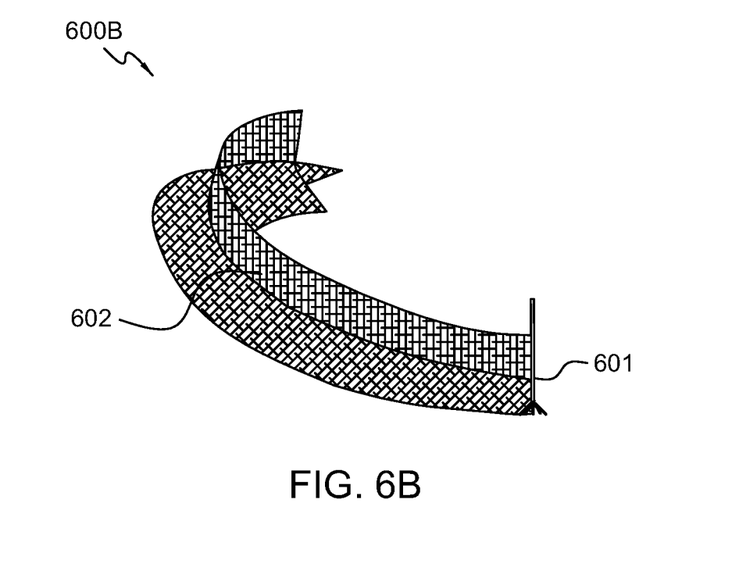

FIGS. 6A and 6B are schematic illustrations 600A and 600B, respectively, of a voxel trail of the catheter produced in accordance with the method of FIG. 4, according to an embodiment. As shown in FIGS. 6A and 6B, voxels are marked wherever the catheter is rendered, creating a voxel trail 602 behind the catheter rendering 601. Since there is no "real" calculation to find the voxels, there is no time delay in the creation of the voxel trail 602.

The voxel trail 602 may be used to define an internal volume within which catheter 14 is positioned, such as a chamber of a heart, blood vessel, or valve. For example, the internal volume may be acquired by bringing the catheter 14 into contact within multiple points on an inner surface of a wall defining the internal volume. The volume outside of the internal volume may be an external volume corresponding to additional anatomical structures, such as a second heart chamber of body organ. The processor 22 may be configured to generate a mesh representing a surface of the internal volume by applying a mesh-generating algorithm to a volume that includes the voxels marked as occupied. The processor 22 may be further configured to display the mesh on the display.

The methods described herein may also comprise algorithms that can be utilized by a skilled software engineer to generate the requisite step-by-step computer codes for implementation of the overall method in a computer system (e.g., a general-purpose computer or a special purpose computer such as the Carto system).

Although the present disclosure relates mainly to a chamber of a heart, it is noted that the techniques described herein may also be used to model any other anatomical or non-anatomical structure. For example, the techniques described herein may be used in depth-sensing applications.

It should be understood that many variations are possible based on the disclosure herein. Although features and elements are described above in particular combinations, each feature or element can be used alone without the other features and elements or in various combinations with or without other features and elements.

What is claimed is:

1. A method performed on a processor, the method comprising:
   receiving a voxel grid comprising a plurality of voxels;
   receiving a plurality of three-dimensional coordinates of a location of a catheter;
   rendering the catheter on a display using the three-dimensional coordinates, wherein the catheter rendering comprises a plurality of shaded pixels;
   identifying the coordinates of one or more voxels of the voxel grid which overlap with at least one shaded pixel, wherein the coordinates (i, j, k) of the voxels which overlap with a pixel of the catheter rendering are determined by dividing a three-dimensional coordinate associated with a shaded pixel by a size of the voxels of the voxel grid; and
   marking the voxels of the voxel grid which overlap with at least one shaded pixel.

2. The method of claim 1, wherein the voxel grid is defined by a central processing unit (CPU) of the processor.

3. The method of define 2, wherein the CPU utilizes a fast anatomical mapping (FAM) algorithm to determine the voxel grid.

4. The method of claim 1, wherein, each time the catheter moves, the processor performs the steps of receiving the plurality of three dimensional-dimensional coordinates, rendering the catheter on the display, identifying the three-dimensional coordinates of one or more voxels which overlap with at least one shaded pixel, and marking the one of more voxels identified as overlapping with at least one shaded pixel.

5. The method of claim 1, wherein the method is conducted using a graphical processing unit (GPU) of the processor.

6. The method of claim 1, wherein the catheter is brought into contact with multiple points of a wall defining an internal volume and the marked voxels define the internal volume.

7. The method of claim 6, wherein the internal volume defines an anatomical structure.

8. The method of claim 7, wherein the anatomical structure is a chamber of the heart.

9. The method of claim 6, further comprising generating a mesh representing a surface of the internal volume by applying a mesh-generating algorithm to the marked voxels.

10. A system comprising:
    a processor configured to:
    receive a voxel grid comprising a plurality of voxels;
    receive a plurality of three-dimensional coordinates of a location of a catheter;
    render the catheter on a display using the three-dimensional coordinates, wherein the catheter rendering comprises a plurality of shaded pixels;
    identify the coordinates of one or more voxels of the voxel grid which overlap with at least one shaded pixel, wherein the coordinates (i, j, k) of the voxels which overlap with a pixel of the catheter rendering are determined by dividing a three-dimensional coordinate associated with a shaded pixel by a size of the voxels of the voxel odd; and mark the voxels of the voxel grid which overlap with at least one shaded pixel; and a display device linked to the processor for displaying the catheter rendering and marked voxels.

11. The system of claim 10, wherein the processor comprises a central processing unit (CPU) and a graphical processing unit (GPU).

12. The system of claim 11, wherein the voxel grid is defined by the CPU of the processor.

13. The system of claim 12, wherein the CPU utilizes a fast anatomical mapping (FAM) algorithm to determine the voxel grid.

14. The system of claim 10, wherein, each time the catheter moves, the processor is configured to receive the plurality of three dimensional-dimensional coordinates, render the catheter on the display, identify the three-dimensional coordinates of one or more voxels which overlap with at least one shaded pixel, and mark the one of more voxels identified as overlapping with at least one shaded pixel.

15. The system of claim 10, wherein the GPU is configured to receive the voxel grid, receive the plurality of three-dimensional coordinates, render the catheter, identify the coordinates of one or more voxels of the voxel grid, and mark the voxels of the voxel grid.

16. The system of claim 10, wherein the marked voxels define an internal volume.

17. The system of claim 16, wherein the internal volume defines an anatomical structure.

18. The system of claim 16, wherein the processor is further configured to apply a mesh-generating algorithm to the marked voxels to generate a mesh representing a surface of the internal volume.

19. A tangible non-transitory computer-readable medium in which program instructions are stored, which, when read by a processor, cause the processor to:

receive a voxel grid comprising a plurality of voxels;

receive a plurality of three-dimensional coordinates of a location of a catheter;

render the catheter on a display using the three-dimensional coordinates, wherein the catheter rendering comprises a plurality of shaded pixels;

identify the coordinates of one or more voxels of the voxel grid which overlap with at least one shaded pixel, wherein the coordinates (i, j, k) of the voxels which overlap with a pixel of the catheter rendering are determined by dividing a three-dimensional coordinate associated with a shaded pixel by a size of the voxels of the voxel grid; and mark the voxels of the voxel grid which overlap with at least one shaded pixel.

* * * * *

UNITED STATES PATENT AND TRADEMARK OFFICE
CERTIFICATE OF CORRECTION

PATENT NO. : 11,974,817 B2
APPLICATION NO. : 17/163978
DATED : May 7, 2024
INVENTOR(S) : Benjamin Cohen et al.

It is certified that error appears in the above-identified patent and that said Letters Patent is hereby corrected as shown below:

On the Title Page

In Item (57), under "ABSTRACT", in Column 2, Lines 4-5, delete "plurality three-dimensional" and insert -- plurality of three-dimensional --, therefor.

In the Specification

In Column 1, Lines 33-34, delete "plurality three-dimensional" and insert -- plurality of three-dimensional --, therefor.

In Column 1, Line 60, delete "is a is a" and insert -- is a --, therefor.

In Column 2, Line 7, delete "rendering the" and insert -- rendering of the --, therefor.

In Column 3, Line 7, delete "referred" and insert -- referred to --, therefor.

In Column 6, Line 32, delete "determines," and insert -- determines --, therefor.

In Column 7, Line 17, delete "405," and insert -- 405. --, therefor.

In Column 7, Line 32, delete "totally" and insert -- total --, therefor.

In the Claims

In Column 8, Line 32, in Claim 3, delete "define 2," and insert -- claim 2, --, therefor.

In Column 8, Line 37, in Claim 4, delete "three dimensional-dimensional" and insert -- three-dimensional --, therefor.

In Column 8, Lines 40-41, in Claim 4, delete "one of more" and insert -- one or more --, therefor.

Signed and Sealed this
Twenty-fourth Day of September, 2024

Katherine Kelly Vidal
*Director of the United States Patent and Trademark Office*

CERTIFICATE OF CORRECTION (continued)
U.S. Pat. No. 11,974,817 B2

In Column 8, Line 44, in Claim 5, delete "graphical" and insert -- graphic --, therefor.

In Column 9, Line 4, in Claim 10, delete "odd;" and insert -- grid; --, therefor.

In Column 9, Line 10, in Claim 11, delete "graphical" and insert -- graphic --, therefor.

In Column 9, Line 19, in Claim 14, delete "three dimensional-dimensional" and insert -- three-dimensional --, therefor.

In Column 9, Line 22, in Claim 14, delete "one of more" and insert -- one or more --, therefor.